US00PP23620P2

(12) United States Plant Patent
Lemon

(10) Patent No.: US PP23,620 P2
(45) Date of Patent: May 21, 2013

(54) GERANIUM PLANT NAMED 'OGLGER5053'

(50) Latin Name: *Pelargonium×domesticum*
Varietal Denomination: Oglger5053

(75) Inventor: David G. Lemon, Lompoc, CA (US)

(73) Assignee: Ecke Geraniums LLC, Encinitas, GA (US)

( * ) Notice: Subject to any disclaimer, the term of this patent is extended or adjusted under 35 U.S.C. 154(b) by 126 days.

(21) Appl. No.: 13/134,378

(22) Filed: Jun. 6, 2011

(51) Int. Cl.
*A01H 5/00* (2006.01)

(52) U.S. Cl.
USPC ..... Plt./331

(58) Field of Classification Search ..... Plt./331
See application file for complete search history.

*Primary Examiner* — June Hwu

(74) *Attorney, Agent, or Firm* — C. A. Whealy

(57) ABSTRACT

A new and distinct cultivar of Regal Geranium plant named 'Oglger5053', characterized by its compact, upright to outwardly spreading and mounded plant habit; freely branching habit; freely flowering habit; and large red purple, light red purple and dark purple-colored flowers.

1 Drawing Sheet

Botanical designation: *Pelargonium×domesticum.*
Cultivar denomination: 'OGLGER5053'.

BACKGROUND OF THE INVENTION

The present invention relates to a new and distinct cultivar of Regal Geranium plant, botanically known as *Pelargonium×domesticum*, and hereinafter referred to by the name 'Oglger5053'.

The new Regal Geranium plant is a product of a planned breeding program conducted by the Inventor in Lompoc, Calif. The objective of the breeding program is to create new freely branching Regal Geranium plants with large and attractive flowers.

The new Regal Geranium plant originated from a cross-pollination made by the Inventor in January, 2003 in Lompoc, Calif. of a proprietary selection of *Pelargonium×domesticum* identified as code number 7394, not patented, as the female, or seed, parent with a proprietary selection of *Pelargonium× domesticum* identified as code number 11088, not patented, as the male, or pollen, parent. The new Regal Geranium plant was discovered and selected by the Inventor as a single flowering plant from within the progeny of the stated cross-pollination in a controlled greenhouse environment in Lompoc, Calif. in March, 2004.

Asexual reproduction of the new Regal Geranium plant by vegetative cuttings in a controlled greenhouse environment in Connellsville, Pa. since July, 2005, has shown that the unique features of this new Regal Geranium plant are stable and reproduced true to type in successive generations.

SUMMARY OF THE INVENTION

Plants of the new Regal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oglger5053'.

These characteristics in combination distinguish 'Oglger5053' as a new and distinct Regal Geranium plant:

1. Compact, upright to outwardly spreading and mounded plant habit.
2. Freely branching habit.
3. Freely flowering habit.
4. Large red purple, light red purple and dark purple-colored flowers.

Plants of the new Regal Geranium differ primarily from plants of the female parent selection in flower color as plants of the female selection have salmon-colored flowers.

Plants of the new Regal Geranium differ primarily from plants of the male parent selection in flower color as plants of the male selection have red and white bi-colored flowers.

Plants of the new Regal Geranium can be compared to plants of *Pelargonium×domesticum* 'Elegance Rose Bicolor', disclosed in U.S. Plant Pat. No. 13,492. In side-by-side comparisons conducted in Encinitas, Calif., plants of the new Regal Geranium differed primarily from plants of 'Elegance Rose Bicolor' in the following characteristics:

1. Plants of the new Regal Geranium had larger flowers than plants of 'Elegance Rose Bicolor'.
2. Plants of the new Regal Geranium and 'Elegance Rose Bicolor' differed in flower color as plants of 'Elegance Rose Bicolor' had red purple and white bi-colored flowers.

BRIEF DESCRIPTION OF THE PHOTOGRAPHS

The accompanying colored photographs illustrate the overall appearance of the new Regal Geranium plant showing the colors as true as it is reasonably possible to obtain in colored reproductions of this type. Colors in the photographs may differ slightly from the color values cited in the detailed botanical description which accurately describe the colors of the new Regal Geranium plant.

The photograph at the bottom of the sheet comprises a side perspective view of a typical flowering plant of 'Oglger5053' grown in a container.

The photograph at the top of the sheet is a close-up view of a typical flowering plant of 'Oglger5053'.

DETAILED BOTANICAL DESCRIPTION

The aforementioned photographs and following observations, measurements and values describe plants grown during the winter and early spring in 15-cm containers in a polyethylene-covered greenhouse in Encinitas, Calif. and under cultural conditions which closely approximate Regal Geranium commercial production. During the production of the plants, day temperatures averaged 18° C., night temperatures averaged 10° C. and light levels averaged 4,000 foot-candles. Plants were 21 weeks old when the photographs and the description were taken. In the detailed description, color references are made to The Royal Horticultural Society Colour Chart, 2007 Edition, except where general terms of ordinary dictionary significance are used.

Botanical classification: *Pelargonium×domesticum* 'Oglger5053'.

Parentage:

*Female, or seed, parent*.—Proprietary selection of *Pelargonium×domesticum* identified as code number 7394, not patented.

*Male or pollen parent*.—Proprietary selection of *Pelargonium×domesticum* identified as code number 11088, not patented.

Propagation:

*Type*.—By vegetative cuttings.

*Time to initiate roots, summer*.—About seven to ten days at soil temperatures of 23° C.

*Time to initiate roots, winter*.—About two weeks at soil temperatures of 23° C.

*Time to produce a rooted young plant, summer*.—About three to four weeks at soil temperatures of 23° C.

*Time to produce a rooted young plant, winter*.—About four to five weeks at soil temperatures of 19.5° C.

*Root description*.—Medium in thickness, fibrous; white in color.

*Rooting habit*.—Moderate branching; medium density.

Plant description:

*General appearance*.—Compact, upright to outwardly spreading and mounding plant habit.

*Growth and branching habit*.—Moderately vigorous growth habit; freely branching habit; about 18 primary lateral branches develop per plant.

*Plant height, to top of umbels*.—About 26 cm.

*Plant height, to top of foliar plane*.—About 19 cm.

*Plant diameter (spread)*.—About 36 cm.

*Lateral branches*.—Length: About 17 cm. Diameter: About 6 mm. Internode length: About 1.5 cm. Texture: Pubescent. Strength: Strong. Color: Close to 144A.

Foliage description:

*Arrangement*.—Alternate; simple.

*Length*.—About 8.4 cm.

*Width*.—About 10 cm.

*Shape*.—Semi-circular; palmately lobed.

*Apex*.—Rounded.

*Base*.—Truncate.

*Margin*.—Bi-serrate.

*Venation pattern*.—Palmate, reticulate.

*Texture, upper and lower surfaces*.—Pubescent.

*Color*.—Developing leaves, upper and lower surfaces: Close to 144A. Fully expanded leaves, upper surface: Close to 137A; venation, close to 137C. Fully expanded leaves, lower surface: Close to 146A; venation, close to 147C.

*Petiole*.—Length: About 4.2 cm. Diameter: About 4 mm. Texture, upper and lower surfaces: Pubescent. Color, upper and lower surfaces: Close to 144A.

Flower description:

*Flower arrangement*.—Nearly round flowers arranged in hemispherical and somewhat loose umbels arising from apical leaf axils; umbels displayed above and beyond the foliar plane on strong peduncles; umbels upright and flowers face upright or outwardly.

*Fragrance*.—None detected.

*Quantity of flowers*.—Freely flowering habit; about five open flowers per umbel; about 28 umbels per plant at one time.

*Flowering season*.—In California, flowering is continuous during the spring and early summer.

*Flower longevity*.—Individual flowers last about five days on the plant; flowers not persistent.

*Umbel height*.—About 6.5 cm.

*Umbel diameter*.—About 8.5 cm.

*Flower diameter*.—About 6 cm.

*Flower depth (height)*.—About 3.8 cm.

*Flower buds*.—Length: About 2 cm. Diameter: About 1 cm. Shape: Elliptical. Color: Close to 75C.

*Petals*.—Quantity per flower and arrangement: Typically five in a single whorl; two upper petals, two lateral petals and one lower petal. Length: Upper petals: About 3.8 cm. Lateral petals: About 3.5 cm. Lower petal: About 3.5 cm. Width: Upper petals: About 3.5 cm. Lateral petals: About 2.5 cm. Lower petal: About 2.2 cm. Shape, all petals: Obovate. Apex, all petals: Rounded. Base, all petals: Attenuate. Margin, all petals: Entire, sinuate. Texture, all petals, upper and lower surfaces: Smooth, glabrous; velvety. Color: When opening, all petals, upper surface: Close to 45C. When opening, all petals, lower surface: Close to 56C. Fully opened, upper petals, upper surface: Apical margins, close to N57A; central margins, close to N57B; central fan-shaped spot, close to N77A; basal margins, close to N57C; at the base, close to NN155D; venation, close to 59B; color does not fade with development. Fully opened, lateral and lower petals, upper surface: Towards the apex, close to N57A; center, close to N57B; towards the base, close to N57C; at the base, close to NN155D; venation, close to 59A to 59B; color does not fade with development. Fully opened, upper petals, lower surface: Close to 56C; central spot, close to 59A to 59B; towards the base, close to NN155D; venation, close to 59B to 59C. Fully opened, lateral and lower petals, lower surface: Close to 56C; towards the base, close to NN155D; venation, close to 59B to 59C.

*Sepals*.—Quantity per flower: Five or six arranged in a single whorl. Length: About 1.8 cm. Width: About 5 mm. Shape: Narrowly elliptical. Apex: Acuminate; apices reflexed. Base: Attenuate. Margin: Entire. Texture, upper and lower surfaces: Pubescent. Color, upper and lower surfaces: Close to 146B.

*Peduncle (umbel stem)*.—Length: About 4.5 cm. Diameter: About 2 mm. Angle: About 30° to 45° from stem axis. Strength: Strong. Texture: Pubescent. Color: Close to 146B.

*Pedicel* (*individual flower stem*).—Length: About 2.6 cm. Diameter: About 1.5 mm. Angle: About 20° to 30° from peduncle axis. Strength: Strong. Texture: Pubescent. Color: Close to 146C.

*Reproductive organs*.—Androecium: Stamen quantity per flower: About six or seven. Anther length: About 3 mm. Anther shape: Narrowly oblong. Anther color: Close to N79B. Pollen amount: Scarce. Pollen color: Close to 181A. Gynoecium: Pistil quantity per flower: One. Pistil length: About 2.1 cm. Stigma shape: Six-parted, star-shaped. Stigma color: Close to 59A. Style length: About 1.2 cm. Style color: Close to 64B. Ovary color: Close to 195A.

*Seed/fruit*.—Seed and fruit development have not been observed.

Disease/pest resistance: Plants of the new Regal Geranium have not been observed to be resistant to pathogens and pests common to Regal Geraniums.

Temperature tolerance: Plants of the new Regal Geranium have been observed to tolerate temperatures ranging from about 4° C. to about 35° C.

It is claimed:

1. A new and distinct Regal Geranium plant named 'Oglger5053' as illustrated and described.

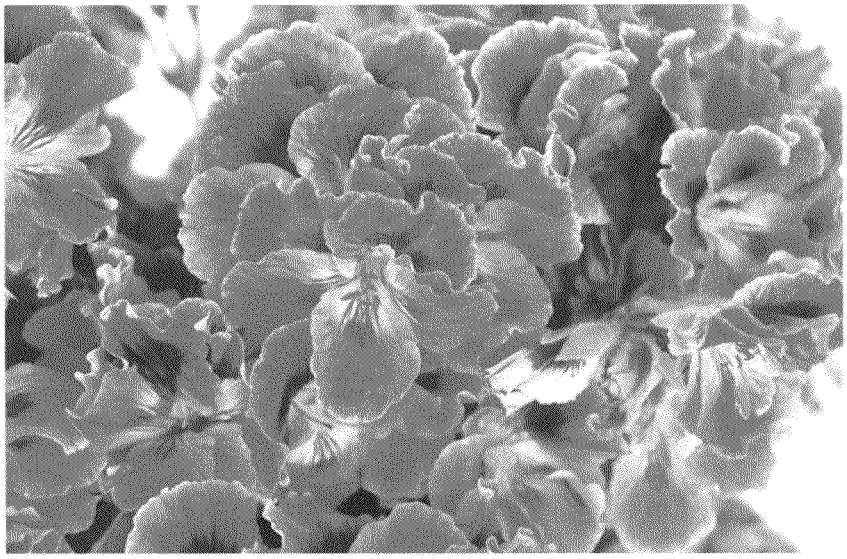
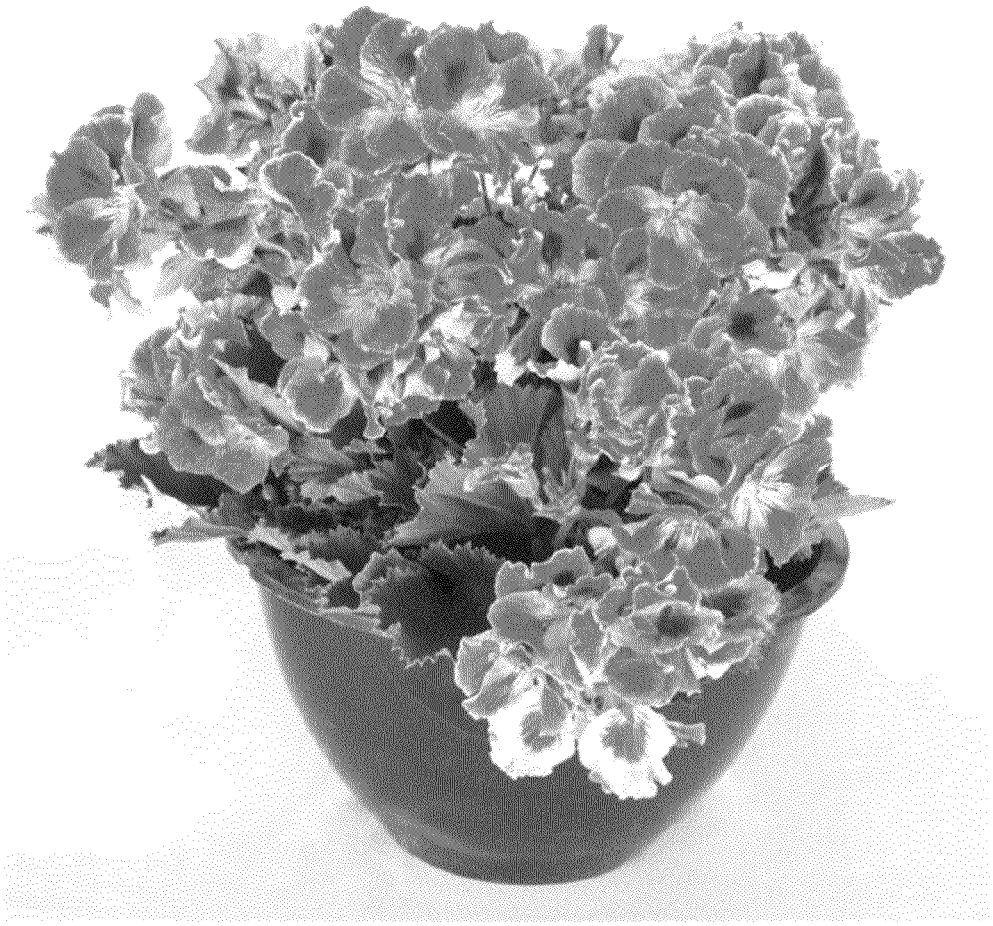

* * * * *